(12) United States Patent
Kvam et al.

(10) Patent No.: US 10,335,078 B2
(45) Date of Patent: Jul. 2, 2019

(54) DEVICE FOR SEPARATION AND COLLECTION OF PLASMA

(71) Applicant: General Electric Company, Schenectady, NY (US)

(72) Inventors: Erik Leeming Kvam, Niskayuna, NY (US); Weston Blaine Griffin, Niskayuna, NY (US); Erin Jean Finehout, Broomfield, CO (US); Ying Mao, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 573 days.

(21) Appl. No.: 14/712,290

(22) Filed: May 14, 2015

(65) Prior Publication Data

US 2016/0029936 A1 Feb. 4, 2016

Related U.S. Application Data

(63) Continuation-in-part of application No. 14/450,585, filed on Aug. 4, 2014, now Pat. No. 9,950,321.

(51) Int. Cl.
*A61B 5/15* (2006.01)
*A61B 5/151* (2006.01)
*C12Q 1/6806* (2018.01)

(52) U.S. Cl.
CPC ........ *A61B 5/150755* (2013.01); *A61B 5/151* (2013.01); *A61B 5/150022* (2013.01);
(Continued)

(58) Field of Classification Search
CPC ............ C12Q 1/6806; A61B 5/150755; A61B 5/15105; A61B 5/151; A61B 5/150068;
(Continued)

(56) References Cited

U.S. PATENT DOCUMENTS 4,066,512 A * 1/1978 Lai ................ B01D 69/144
435/10
5,010,629 A 4/1991 Hirzel
(Continued)

FOREIGN PATENT DOCUMENTS

EP 2375249 A2 10/2011
GB 2151943 A 7/1985
(Continued)

OTHER PUBLICATIONS

Weston Blaine Griffin et al., filed Aug. 4, 2014, U.S. Appl. No. 14/450,585.
(Continued)

*Primary Examiner* — Krishnan S Menon
*Assistant Examiner* — Waqaas Ali
(74) *Attorney, Agent, or Firm* — Eversheds Sutherland (US) LLP

(57) ABSTRACT

A method for separating and collecting cell-free plasma by finger stick that minimizes contamination with genomic DNA from a donor. The method comprising placing a tourniquet on one of the digits of the donor's finger to apply pressure, lancing the digit to create an incision in the digit, and collecting blood from the incision from the incision site. The collected blood is placed on a separation membrane wherein the separation membrane is in contact with a collection membrane and both the separation and collection membrane are inserted into a substrate configured to provide overlap between the membranes. A kit and instructions for carrying out the method is also provided.

12 Claims, 7 Drawing Sheets

(52) U.S. Cl.
CPC .... *A61B 5/150068* (2013.01); *A61B 5/15105* (2013.01); *A61B 5/150343* (2013.01); *A61B 5/15142* (2013.01); *C12Q 1/6806* (2013.01)

(58) Field of Classification Search
CPC ........ A61B 5/150022; A61B 5/150343; A61B 5/15142
See application file for complete search history.

(56) References Cited

U.S. PATENT DOCUMENTS

| | | | |
|---|---|---|---|
| 5,133,730 | A | 7/1992 | Biro et al. |
| 5,518,006 | A | 5/1996 | Mawhirt et al. |
| 5,560,830 | A | 10/1996 | Coleman et al. |
| 5,876,926 | A | 3/1999 | Beecham |
| 5,893,870 | A | 4/1999 | Talen et al. |
| 5,916,521 | A * | 6/1999 | Bunce ................ G01N 33/5002 422/422 |
| 6,106,732 | A | 8/2000 | Johnston et al. |
| 7,744,820 | B2 | 6/2010 | Togawa et al. |
| 7,794,720 | B2 | 9/2010 | Wilson |
| 2009/0177224 | A1* | 7/2009 | Naghavi .......... A61B 5/150022 606/203 |
| 2009/0198152 | A1 | 8/2009 | Kim |
| 2012/0024788 | A1 | 2/2012 | Kelso et al. |
| 2012/0220047 | A1 | 8/2012 | Seifried et al. |
| 2012/0301893 | A1 | 11/2012 | Siciliano et al. |
| 2013/0334139 | A1 | 12/2013 | Blickhan et al. |
| 2015/0031035 | A1 | 1/2015 | Kvam et al. |
| 2015/0031086 | A1 | 1/2015 | Heller et al. |

FOREIGN PATENT DOCUMENTS

| | | |
|---|---|---|
| GB | 2481221 A | 12/2011 |
| WO | 1997018036 | 5/1997 |
| WO | 03/095969 A2 | 11/2003 |
| WO | 2004033101 A1 | 4/2004 |
| WO | 2007000048 | 1/2007 |
| WO | 2007/068811 A1 | 6/2007 |
| WO | 2007068811 A1 | 6/2007 |
| WO | 2014018903 A1 | 1/2014 |
| WO | 2014023756 A1 | 2/2014 |
| WO | 2015086261 A1 | 6/2015 |

OTHER PUBLICATIONS

International Search Report and Written Opinion regarding International Application No. PCT/EP2016/060947, dated Oct. 19, 2016, 13 pages.

Nabatiyan et al., "Membrane-based plasma collection device for point-of-care diagnosis of HIV", Journal of Virological Methods, vol. 173, pp. 37-42, 2011.

Hartford, "A Preanalytic Blood Separation and Metering System for Qualitative and Quantitative Lateral Flow Biosensors", Medical Device & Diagnostic Industry—IVD, Jun. 2013, 8 Pages.

Mezitis et al., "Self-monitoring of blood glucose: Tourniquet method", Diabetes Care, vol. 10, No. 6, pp. 793-794, Nov./Dec. 1987.

EP Office Action for corresponding application No. 16724017.5 dated Aug. 21, 2018; 6 pages.

Hosono et al., "Unbiased Whole-Genome Amplification Directly From Clinical Samples", Genome Research, vol. No. 13, Issue No. 5, pp. 954-964, May 2003.

Wu et al., "A Simple Method to Elute Cell-Free HIV from Dried Blood Spots Improves their Usefulness for Monitoring Therapy", Journal of Clinical Virology, vol. No. 65, pp. 38-40, Apr. 2015.

PCT Search Report and Written Opinion issued in connection with Related Application No. PCT/EP2015/067888 dated Oct. 26, 2015.

U.S. Restriction Requirement issued in connection with Related U.S. Appl. No. 14/450,585 dated Mar. 22, 2016.

* cited by examiner

DEVICE FOR SEPARATION AND COLLECTION OF PLASMA

CROSS-REFERENCE TO RELATED APPLICATIONS

This application is a continuation in part of pending U.S. application Ser. No. 14/450,585 filed on Aug. 4, 2014.

BACKGROUND

The present invention relates to a medical device and consumables, and more particularly to a kit and directions used for separating and collecting cell-free plasma from finger stick blood samples to be used for genomic testing.

Typically, centrifugation is used to separate and collect cell-free plasma from blood samples; however, centrifugation is not always available at the point-of-collection and is not convenient for small blood volumes collected by finger stick. For small blood volumes, filtration membranes can be used to separate and collect plasma from blood samples. In a common method, a single filtration membrane is used for the separation and collection of plasma. In such method, blood samples may be applied to one end of the filtration membrane and as the blood sample flows through, blood cells may be separated from the plasma based on the size of the membranes pores. After filtration, the plasma containing portion of the membrane must be separated or severed from the blood cell-containing portion of the membrane, thereby necessitating an additional step of cutting the membrane prior to downstream plasma analysis. Furthermore, this single membrane approach may prevent using different materials and/or chemistries in the membranes for the separation and collection of plasma.

In another method, two separate membranes are used for the separation and collection of plasma by lateral flow. Specifically, a first membrane is used to filter and separate blood cells and a second membrane accepts or transfers the resulting cell-free plasma. These membranes may be arranged such that a distal end of the first membrane contacts a proximal end of the second membrane to facilitate the separation of blood cells via the first membrane and the collection of plasma via the second membrane by capillary flow.

Typically, devices for holding two membranes end-to-end with a minimal, but reproducible, overlap require a superior manufacturing tolerance that may not be compatible with low-cost manufacturing methods such as injection molding. Also, it may be difficult to apply uniform pressure at a contact area of the membranes to ensure consistent transfer of plasma from the separation membrane to the collection membrane without damaging the membranes.

With any blood collection and separation methods, there exists the potential to release genomic DNA from blood cells during the sample collection phase or separation phase. For membrane-based filtration and separation, this released genomic DNA is typically smaller than the pore size of the filtration membrane, and thus can flow with the plasma fraction. In downstream genomic analyses, this genomic DNA released ex vivo during sample collection and separation represents a contaminant species. This fact is especially pertinent to the genetic analysis of cell-free DNA, which is naturally released from cells into systemic circulation inside the body. Thus, the contamination of plasma with genomic DNA released ex vivo by non-optimal blood collection and separation can affect the desired analysis of natural cell-free DNA species released in vivo.

Thus, there is a need for an improved device or consumable that minimizes the release of genomic DNA from blood cells and facilitates proper holding and accurate positioning of two membranes used in plasma separation and collection. Moreover, there is a need for proper implementation of devices or consumable with finger stick blood samples such that DNA contamination is minimized during the process of preparing plasma from finger prick whole blood.

BRIEF DESCRIPTION

In one embodiment, provided is a method for isolating cell-free plasma from finger stick whole blood that is not substantially contaminated with genomic DNA. The method comprises placing a tourniquet on one of the digits of the donor's finger to apply pressure, lancing the digit to create an incision in the digit, and collecting blood from the incision from the incision site. The collected blood is placed on a separation membrane wherein the separation membrane is in contact with a collection membrane and both the separation and collection membrane are inserted into a substrate configured to provide overlap between the membranes In some embodiments, the device or consumable for isolating plasma comprises a substrate for positioning a separation membrane and a collection membrane for separating and collecting plasma. The substrate includes an inner flexure disposed proximate to a first peripheral portion of the substrate. The inner flexure is formed from a plurality of first slots in the substrate. The substrate further includes an outer flexure disposed surrounding at least a portion of the plurality of first slots. The outer flexure is formed from a plurality of second slots in the substrate.

In another embodiment, a kit for isolating cell-free plasma from finger stick whole blood, wherein the collected plasma is not substantially contaminated with genomic DNA is provided. The kit comprises a device for separating and collecting plasma, a lancet, a capillary or sample transfer tube, and a tourniquet material. The tourniquet material includes a rubber band, elastic band, or any other flexible material of the like that can be generally used to create a tourniquet. The device includes a separation membrane, a collection membrane, and a substrate.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

Embodiments discussed herein disclose a new device for facilitating plasma separation and collection from blood samples. In certain embodiments, the device includes one piece substrate having an outer flexure and an inner flexure, a separation membrane, and a collection membrane. The inner flexure is formed from a plurality of first slots and the outer flexure is formed from a plurality of second slots. The inner flexure is configured to align a distal end of the separation membrane under a distal end portion of the outer flexure. The outer and inner flexures are further configured to align a proximal end of the collection membrane under the distal end portion of the outer flexure and a distal end portion of the inner flexure such that the proximal end of the collection membrane has a defined overlapping contact area with the distal end of the separation membrane. The overlapping contact area between the two membranes within the substrate facilitates proper separation and collection of plasma from the blood samples.

Figure 1:
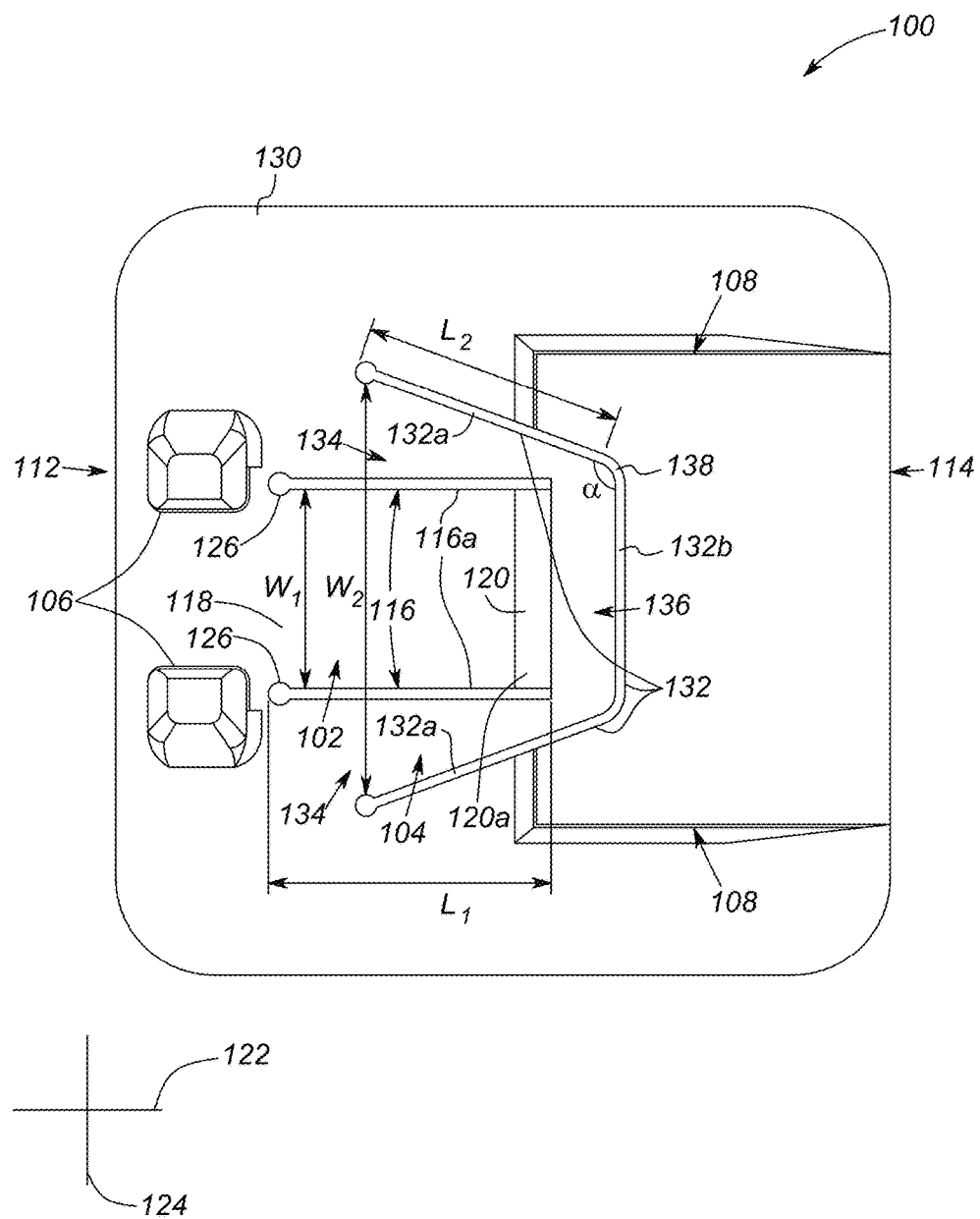
FIG. 1 illustrates a top view of a substrate in accordance with one exemplary embodiment.
Figure 2:
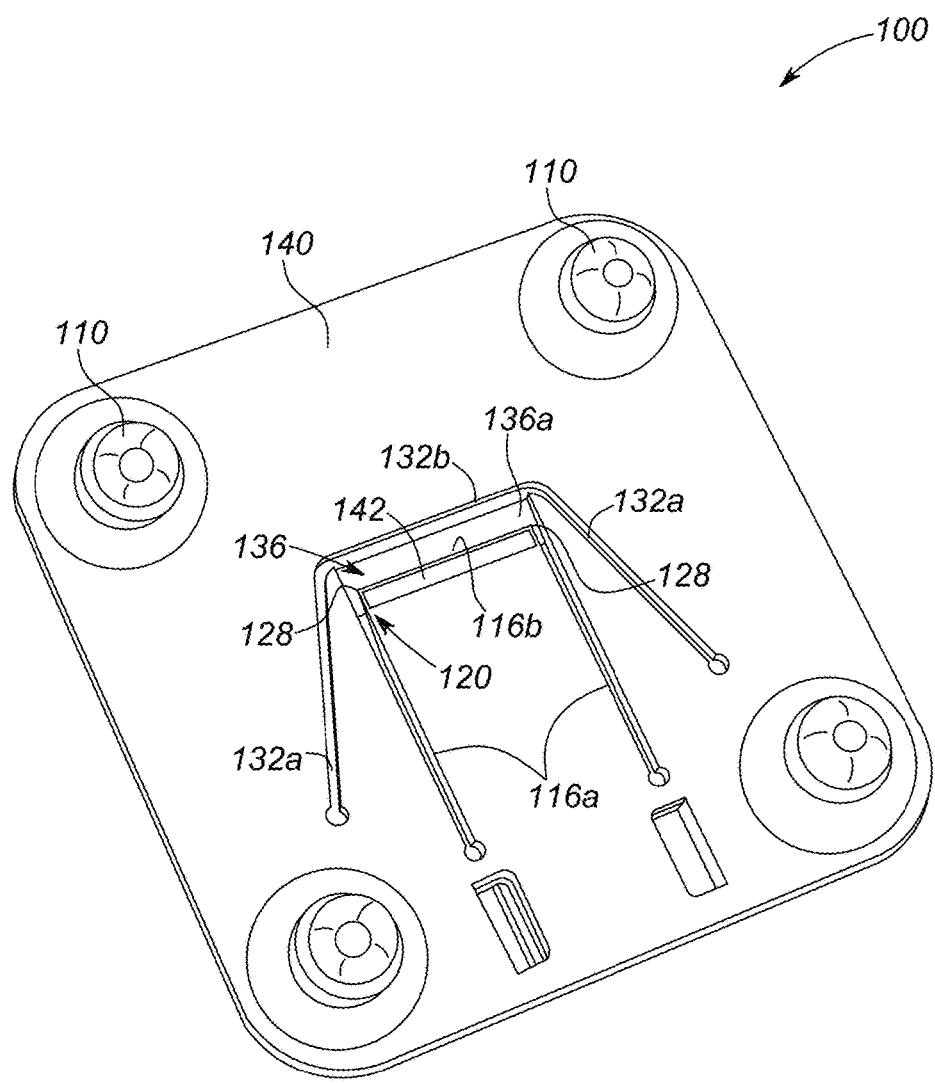
FIG. 2 illustrates a bottom view of a substrate in accordance with one exemplary embodiment.

FIG. 1 represents a top view of a substrate 100 in accordance with one exemplary embodiment of the device. The substrate 100 includes an inner flexure 102 and an outer flexure 104. The substrate 100 further includes a plurality of holding mechanism 106, a plurality of guiding mechanism 108, and a plurality of fixtures 110 (as shown in FIG. 2).

Figure 3:
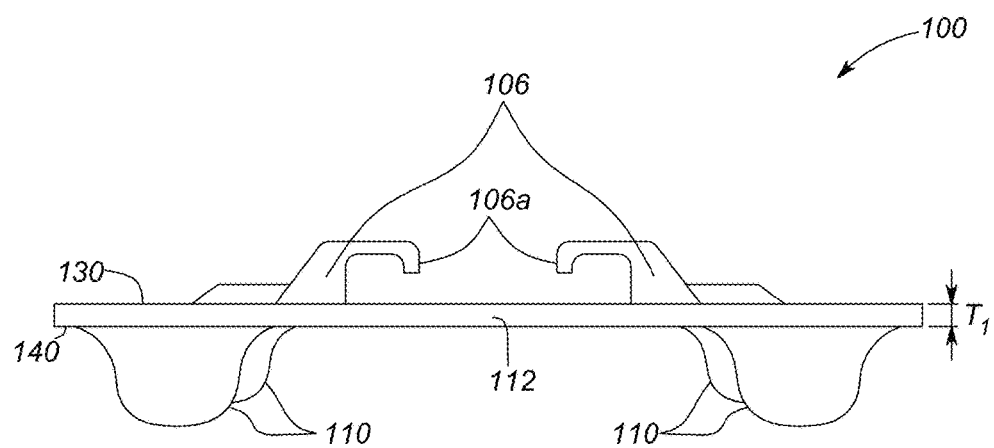
FIG. 3 illustrates a side view of a substrate in accordance with one exemplary embodiment.

The substrate 100 is a base member configured to receive, hold, support, and align at least two membranes used in separation and collection of plasma from blood samples. In one embodiment, the substrate 100 has a square shape with curved edges and includes a first peripheral portion 112 and a second peripheral portion 114 disposed opposite to the first peripheral portion 112. The substrate 100 has a polymer material such as polypropylene, nylon (polyamide), high density polyethylene (HDPE), and polyetheretherketone (PEEK). In one embodiment, the substrate 100 may be manufactured using an injection molding technique and has a uniform thickness "$T_1$" (as shown in FIG. 3) with minimal tolerance to align the two membranes. In certain other embodiments, the substrate 100 may have different shape such as circular, oval, rectangle, and the like. Similarly, the substrate 100 may have varied thickness "$T_1$" depending on the application and design criteria.

In one embodiment, the inner flexure 102 is located proximate to the first peripheral portion 112 and formed from a plurality of first slots 116 in the substrate 100. Specifically, the inner flexure 102 is defined by a portion of the substrate 100 bounded by the plurality of first slots 116. The plurality of first slots 116 includes a plurality of first sub-slots 116a and a first mid-slot 116b (as shown in FIG. 2). The first mid-slot 116b is located at a first distal end portion 120 of the inner flexure 102 and connected to a distal end 128 (as shown in FIG. 2) of each first sub-slot 116a. A proximal end 126 of the plurality of first sub-slots 116a is proximate to the first peripheral portion 112. In one embodiment, the plurality of first sub-slots extends along a pre-determined angle relative to the first mid-slot 116b and the first mid-slot 116b extends along a transverse direction 124. In one embodiment, the pre-determined angle is about 90 degrees. In certain other embodiments, the plurality of first sub-slot 116a may extend along a longitudinal direction 122 and are parallel to each other.

The inner flexure 102 has geometry of a beaker turned on its one side, and has a thickness equal to the thickness "$T_1$" of the substrate 100. The geometry of the inner flexure 102 varies based on a length "$L_1$" of the plurality of first slots 116 and a width "$W_1$" of the inner flexure 102. Similarly, the thickness of the inner flexure 102 may vary depending on the application and design criteria. The inner flexure 102 has a first stiffness "$S_1$" depending on the geometry and thickness of the inner flexure 102. The stiffness "$S_1$" may be controlled by either increasing or decreasing the width "$W_1$", length "$L_1$", and thickness of the inner flexure 102. In one exemplary embodiment, the inner flexure 102 has a relatively longer length "$L_1$", a relatively narrow width "$W_1$", and thickness "$T_1$" of the substrate 100 to obtain a substantially lesser stiffness "$S_1$" in comparison with a stiffness of the outer flexure 104. In another embodiment, the inner flexure 102 may have a relatively longer length "$L_1$", a relatively narrow width "$W_1$", and a relatively thinner thickness in comparison with the thickness "$T_1$" of the substrate 100 to obtain a substantially lesser stiffness "$S_1$" in comparison with a stiffness of the outer flexure 104.

In the illustrated embodiment, the first distal end portion 120 has a first tapered portion 120a. The first tapered portion 120a is formed on a top surface 130 of the substrate 100 corresponding to the first distal end portion 120. The first tapered portion 120a is configured to allow smooth bending of membranes (not shown in FIG. 1) along the first mid-slot 116b. In certain other embodiments, the first distal end portion 120 may have a first rounded portion having an arc shaped profile to allow smooth bending of membranes along the first mid-slot 116b. The first distal end portion 120 may have different profile depending on the application and design criteria.

In one embodiment, the outer flexure 104 is located surrounding a portion of the plurality of first slots 116 and formed from a plurality of second slots 132 in the substrate 100. Specifically, the outer flexure 104 is defined by another portion of the substrate 100 bounded between the plurality of first slots 116 and the plurality of second slots 132. The outer flexure 104 has a second proximal end portion 134 and a second distal end portion 136. In the illustrated embodiment, the outer flexure 104 has a trapezoidal geometry and has a thickness equal to the thickness "$T_1$" of the substrate 100. The geometry of the outer flexure 104 may vary based on a length "$L_2$" of the plurality of second slots 132 and a width "$W_2$" of the outer flexure 104. Similarly, the thickness of the outer flexure 104 may vary depending on the application and design criteria.

The plurality of second slots 132 includes a plurality of second sub-slots 132a and a second mid-slot 132b. The plurality of second sub-slots 132a surrounds a portion of the plurality first sub-slots 116a and the second mid-slot 132b is located near the first mid-slot 116b. Further, the second mid-slot 132b is connected to a distal end 138 of each second sub-slot 132a. In the illustrated embodiment, the second mid-slot 132b extends along the transverse direction 124 and each second sub-slot 132a extends at a predetermined angle "α" relative to the second mid-slot 132b. In one embodiment, the pre-determined angle "α" is greater than or equal to 90 degrees. In certain other embodiments, each second sub-slot 132a may extend in the longitudinal direction 122 and in such embodiments the plurality of second sub-slots 132a may be parallel to each other.

The outer flexure 104 has a second stiffness "$S_2$" depending on the geometry and thickness of the outer flexure 104. In one embodiment, the first stiffness "$S_1$" is lesser than the second stiffness "$S_2$". The stiffness "$S_1$" and "$S_2$" may change depending on the geometry and thickness of the respective flexures 102, 104. The stiffness "$S_2$" may be controlled by either increasing or decreasing the width "$W_2$", length "$L_2$", and thickness of the outer flexure 104. Specifically, the width "$W_2$" may be controlled by varying the pre-determined angle "a" and may be controlled by varying the length of the second mid-slot 132b. In one exemplary embodiment, the outer flexure 104 has a wider width "$W_2$", a shorter length "$L_2$", and similar thickness to obtain a substantially greater stiffness "$S_2$" in comparison with the stiffness "$S_1$" of the inner flexure 102. For example, the stiffness "$S_1$" being less than "$S_2$" may be a measure by stiffness in the flexures as determined by the degree of deflection when a load is applied to the substrate at the respective mid-slots 116b, 132b by the inner and outer flexures 102, 104.

In the illustrated embodiment, the second distal end portion 136 has a second tapered portion 136a (as shown in FIG. 2). The second tapered portion 136a is formed on a bottom surface 140 (as shown in FIG. 2) of the substrate 100 corresponding to the second distal end portion 136. The second tapered portion 136a is configured to reduce bending of the membranes (not shown in FIG. 1) along the second mid-slot 132b. In certain other embodiments, the second distal end portion 136 may have a second rounded portion having an arc shaped profile to allow smooth bending of membranes along the second mid-slot 132b. The second distal end portion 136 may have different profile depending on the application and design criteria.

The plurality of holding mechanism 106 is disposed on the top surface 130. Specifically, the holding mechanism 106 is located between the first peripheral portion 112 and the first proximal end portion 118. In the illustrated embodiment, the holding mechanism 106 is a clip having an arch shaped design. In certain other embodiments, the holding mechanism 106 may be hooks, clasps, adhesives, and the like. The holding mechanism 106 may be configured to hold and align a separation membrane (not shown in FIG. 1) to position along the inner flexure 102 and beneath the outer flexure 104. Further, the clip of the holding mechanism 106 may prevent the separation membrane 152 being cantilevered at the proximal end 156.

The plurality of guiding mechanism 108 is disposed on the top surface 130. Specifically, the guiding mechanism 108 is located surrounding a portion of the plurality of second slots 132 and proximate to the second peripheral portion 114. In the illustrated embodiment, the guiding mechanism 108 is a ridge having protrusion. In certain other embodiments, the guiding mechanism 108 may be printed lines, grooves, and the like. The guiding mechanism 108 may be configured to support and guide a collection membrane (not shown in FIG. 1) to position beneath the outer flexure 104. The guiding mechanism 108 may also be configured to limit any motion of the separation membrane when the membrane is wetted.

The plurality of fixtures 110 is disposed on the bottom surface 140 so as to ensure a gap between the substrate 100 and a surface (not shown) upon which the substrate is placed. Specifically, the plurality of fixtures 110 is located at all corners of the substrate 100. In the illustrated embodiment, the fixture 110 is a circular support structure. In certain other embodiments, the fixture 110 may be wedges, blocks, and the like. The fixture 110 may be configured to support the substrate 100 over any surface.

FIG. 2 represents a bottom view of the substrate 100 in accordance with the exemplary embodiment of FIG. 1. In the illustrated embodiment, the outer flexure 104 includes the second distal end portion 136 overlapping with a fraction 142 of the first distal end portion 120 of the inner flexure 102. In one embodiment, the first tapered portion 120a and the second tapered portion 136a typically forms a skive cut (i.e. an angled cut or an angled slot) between the inner flexure 102 and the outer flexure. The first tapered portion 120a (as shown in FIG. 1) and the second tapered portion 136a have a complementary profile so as to reduce bending of the membranes (not shown in FIG. 2) along the skive cut via the mid slots 116b, 132b. In another embodiment, the first curved portion and second curved portion may have a complementary profile. In certain other embodiments, the second distal end portion 136 may not have overlapping fraction 142 with the first distal end portion 120. In such embodiments, a contact area (not shown in FIG. 2) of the membranes may be defined by a width of the distal end portion 136 and a width of the mid-slot 116b of the outer flexure 104. Further, the stiffness "$S_1$", $S_2$" of the flexures 102, 104 may be adjusted based on a thickness of the membranes.

FIG. 3 represents a side view of the substrate 100 in accordance with the exemplary embodiments of FIGS. 1 and 2. In the illustrated embodiment, the substrate 100 includes the plurality of holding mechanism 106 is an arch shaped clip 106a disposed proximate to the first peripheral portion 112 and on the top surface 130 of the substrate 100. The plurality of fixtures 110 is disposed at all corners and on the bottom surface 140 of the substrate 100. Further, the substrate 100 has the uniform thickness "$T_1$".

Figure 4:
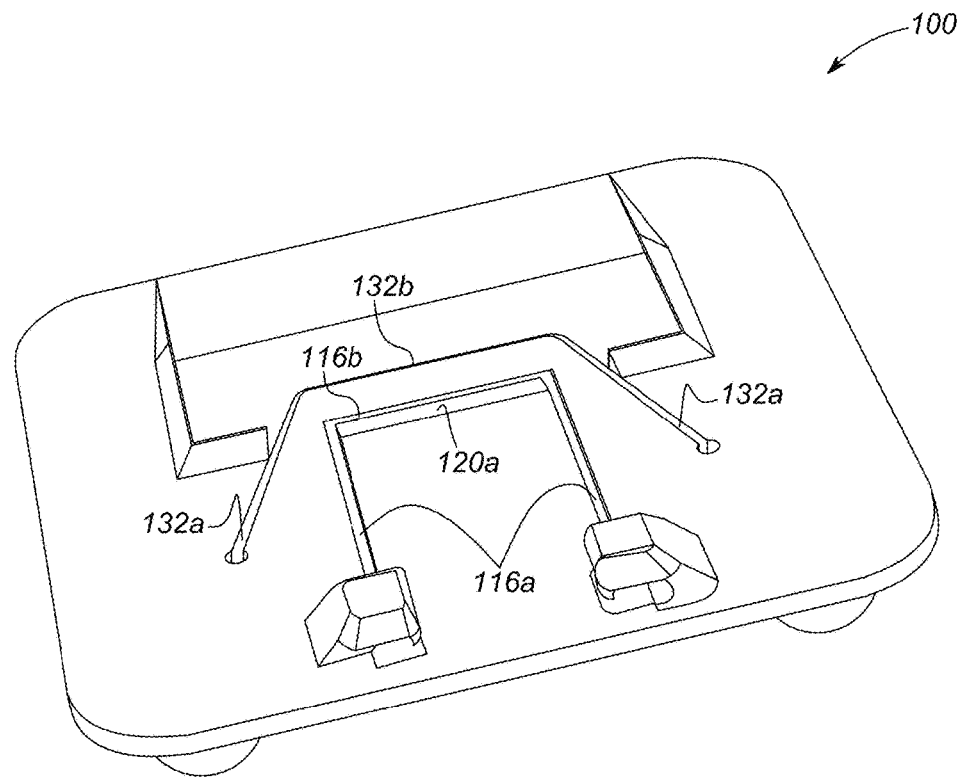
FIG. 4 represents a perspective top view of a substrate in accordance with the exemplary embodiments of FIGS. 1, 2, and 3.

FIG. 4 represents a perspective top view of the substrate 100 in accordance with the exemplary embodiments of FIGS. 1, 2, and 3. In the illustrated embodiment, the inner flexure 102 includes the plurality of first sub-slots 116a and the first mid-slot 116b. The first distal end portion 120 of the inner flexure 102 includes the first tapered portion 120a. The outer flexure 104 includes the plurality of second sub-slots 132a and the second mid-slot 132b.

Figure 5:
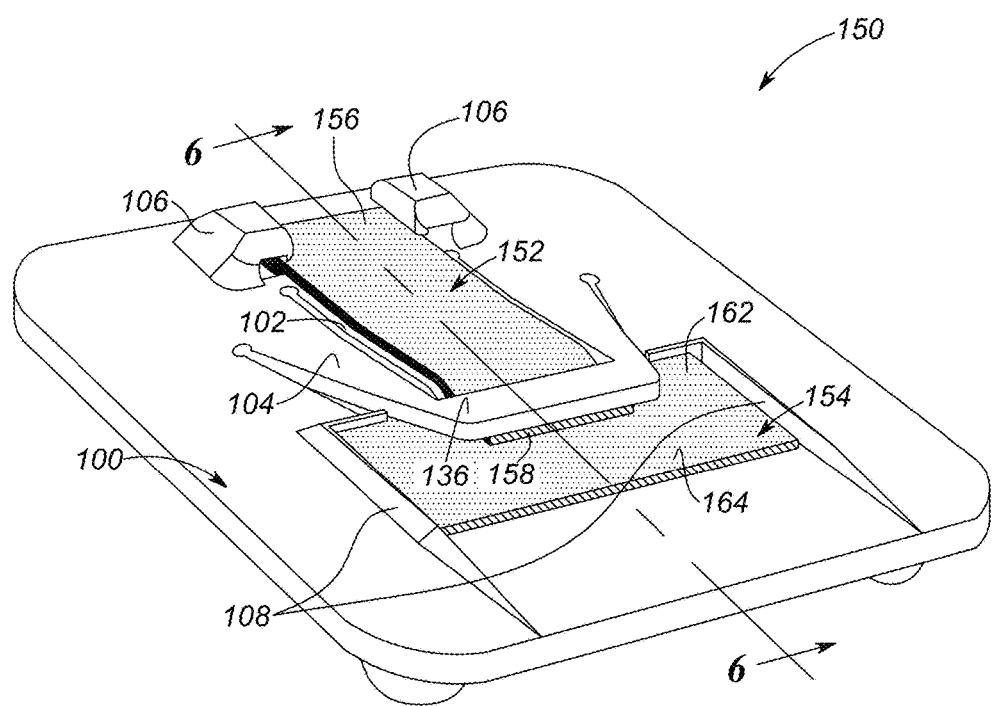
FIG. 5 represents a perspective top view of a device having the substrate in accordance with the exemplary embodiment of FIG. 4.

FIG. 5 represents a perspective top view of a device 150 in accordance with the exemplary embodiment of FIG. 4. The device 150 includes the substrate 100, a separation membrane 152, and a collection membrane 154. The device 150 may be configured to receive the blood samples obtained via a finger prick or a heel prick for separation and collection of plasma. The device 150 may be configured for a horizontal blood flow or a vertical blood flow.

In one embodiment, the separation membrane 152 is a membrane, configured to remove cells from the blood samples. The separation membrane 152 may include suitable materials such as cellulose, a glass fiber, a cellulose acetate, a poly vinyl pyrrolidone, a polysulfone, a polyethersulfone, a polyester or combinations of these materials. The separation membrane 152 may be designed to have a geometry compatible with the geometry of the substrate 100, specifically, the geometry of the inner flexure 102 of the substrate 100. In the illustrated embodiment, the separation membrane 152 is of rectangular shape and includes a proximal end 156 and a distal end 158. The separation membrane 152 is disposed over the inner flexure 102. The distal end 158 is disposed under the outer flexure 104 and the proximal end 156 is disposed beneath the plurality of the holding mechanism 106. The holding mechanism 106 having the arch shaped clip 106a may hold the separation membrane 152 by maintaining a wider gap between the separation membrane 152 and the substrate 100 or the inner flexure 102. Thus, the holding mechanism 106 having the arch shaped clip 106a may avoid the blood samples to spread on the device 150 or the substrate 100 or the holding mechanism 106 from the separation membrane 152 due to surface tension and/or capillary force induced typically in the gap.

Figure 6:
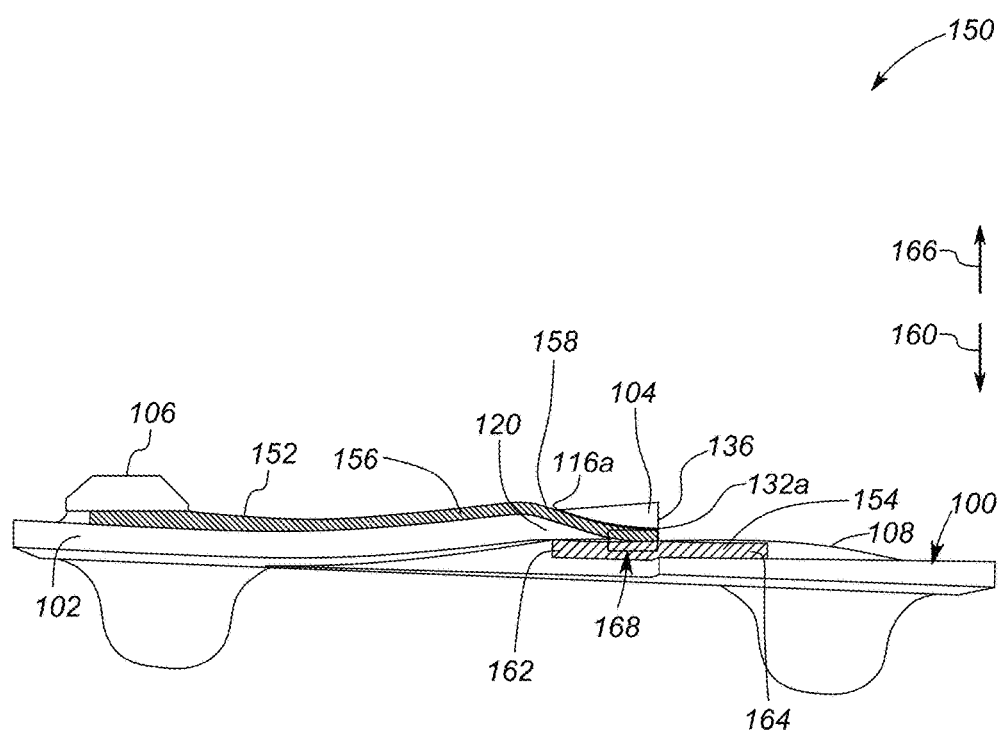
FIG. 6 represents a sectional side view of the device in accordance with the exemplary embodiment of FIG. 5.

In one embodiment, the collection membrane 154 is a chemically treated membrane, configured to enhance stability of components e.g. plasma, in the blood samples. The collection membrane 154 may include suitable materials such as cellulose, a glass fiber, a cellulose acetate, a poly vinyl pyrrolidone, a polysulfone, a polyethersulfone, polyester, or combinations of these materials. In the illustrated embodiment, the collection membrane 154 is of rectangular shape and includes a proximal end 162 and a distal end 164. The collection membrane 154 is disposed under the outer flexure 104 and inner flexure 102. Specifically, the proximal end 162 is disposed under the second distal end portion 136, the first distal end portion 120 (as shown in FIG. 4), and the distal end 158 of the separation membrane 154, and the distal end 164 is disposed along the plurality of the guiding mechanism 108. Upon positioning the membranes 152, 154 on the substrate 100, an overlapping contact area 168 (as shown in FIG. 6) is formed between the proximal end 162 of the collection membrane 154 and the distal end 158 of the separation membrane 152. In one embodiment, the overlapping contact distance in the longitudinal direction 122 is in a range from about 1 mm to about 2 mm. The separation membrane 152 is about 8 mm wide in the transverse direction. The overlapping contact area 168 is defined by the overlapping contact distance and the width of the separation membrane 152 and is in the range from about 8 mm² to about 16 mm². The outer flexure 104 having the stiffness "$S_2$" is configured to apply pressure on membranes 152, 154 about the overlapping contact area 168 and hold the membranes 152, 154 together at their respective ends 158, 162.

FIG. 6 represents a sectional side view along an axis 6-6 of the device 150 in accordance with the exemplary embodiment of FIG. 5.

The separation membrane 152 is introduced along the inner flexure 102 via the plurality of holding mechanism 106, which is configured to hold and align the separation membrane 152 to position along the inner flexure 102. Further, the inner flexure 102 is displaced, or pressed in a first direction 160, (e.g. downward direction) such that the distal end 158 of the separation membrane 152 may be inserted beneath the second distal end portion 136 of the outer flexure 104 via the first mid-slot 116b of the inner flexure 102.

The collection membrane 154 is placed along the plurality of guiding mechanism 108, which is configured to support the collection membrane 154 to position towards the outer flexure 104. Further, the outer flexure 104 and inner flexure 102 is displaced or pushed in a second direction 166, (e.g. upward direction) such that the proximal end 162 of the collection membrane 154 may be inserted beneath the second distal end portion 136 via the second mid-slot 132b, and the first distal end portion 120. The proximal end 162 of the collection membrane 154 has the overlapping contact area 168 with the distal end 158 of the separation membrane 152. The outer flexure 104 and inner flexure 102 is released from the pushed position to an initial rest position so as to apply pressure on the separation membrane 152 and collection membrane 154 about the overlapping contact area 168. In the illustrated embodiment, the inner flexure 102 and outer flexure 104 apply uniform pressure in the transverse direction 124 across the distal end 158 of the separation membrane 152 and proximate to the proximal end 162 of the collection membrane 154 to facilitate proper plasma separation and collection from the blood samples.

During usage of the device 150, the blood samples (not shown in FIG. 6) may be applied on the proximal end 156 of the separation membrane 152. The blood samples may flow in the longitudinal direction 122 along the separation membrane 152 where the blood cells are retained. The blood samples may reach the overlapping contact area 168 where the plasma in the blood samples is transferred from the separation membrane 152 into the collection membrane 154. Later, the plasma is stabilized as it moves along the collection membrane 154.

In accordance with embodiments discussed herein, a single piece substrate facilitates accurate positioning of the membranes. The substrate with flexures design and homogenous material provides uniform pressure at an overlapping contact area of the membranes. The arc shaped clips avoids damaging the membranes. Due to less tolerance requirement, the substrate may be easy to use and manufacture.

In accordance with other embodiments, a method is provided to provide for a protocol wherein the blood collected is for cell-free DNA (cfDNA) analysis such that genomic DNA (gDNA) is limited in the separated plasma fraction. Cell-free DNA is defined as DNA with a low-molecular weight DNA having an average molecular weight of approximately less than or equal to 1 kB, and that is substantially free of genomic DNA (gDNA) defined as having a higher average molecular weight approximately greater than 10 kB. Substantially free is defined as having less than approximately 10% gDNA present in collected cfDNA sample. As such, Proper analysis of cell-free DNA requires very low presence of genomic DNA in a sample. Significant contamination with genomic DNA can impair the sensitivity of cell-free DNA assays. This is typically avoided with venous blood by centrifuging the sample immediately after collection or by using proprietary stabilization reagents. However, neither solution is applicable to finger stick blood, which is collected in very small volumes However, collecting cfDNA from finger stick blood is not a routine process. It was found that standard milking or squeezing of the finger, often used in finger stick blood sampling, releases significant genomic DNA contamination into the collected plasma fraction. In one embodiment, it was found that, a controlled tourniquet type pressure applied to the finger prevents genomic DNA contamination of the fractionated plasma sample. Without limiting to a specific hypothesis, it appears that building capillary bed pressure using a tourniquet can eliminate gDNA contamination of the finger stick plasma sample.

As such, a method for collecting finger stick blood, for downstream genetic analysis of cell-free DNA, is possible by applying a tourniquet to increase capillary pressure in a finger. The tourniquet maybe comprised of a rubber band or elastic material placed around the first, second, or third digit of a subject's hand. In one embodiment, the method, as illustrated in flow chart of FIG. 7 may include placing a tourniquet on one of the digits of the donor's finger to apply pressure (701) and lancing the digit to create an incision in the digit (702). The method may also include optionally removing the first blood immediately after lancing while still applying pressure.

Figure 7:
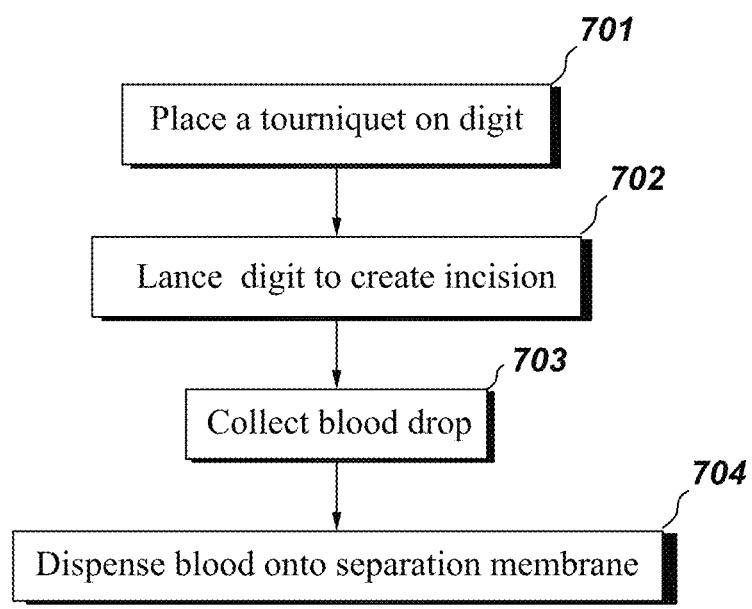
FIG. 7 is a flow chart representative of the method of cell-free plasma collection.

As shown further in FIG. 7, the method also includes collecting blood from the incision by holding a capillary tube against a blood drop formed from the incision site (703) and dispersing the collected blood from the capillary tube onto a separation membrane (704). In certain embodiments, the separation membrane is in contact with a collection membrane and both the separation and collection membrane are inserted into a substrate configured to provide overlap between the said membranes.

In certain embodiments, a kit may also be provided to allow collection, isolation, and, optionally, transport of cell-free plasma for downstream analysis of cell-free DNA. In certain embodiments, the kit may include the device for separating and collecting plasma, the device comprising a separation membrane, a collection membrane, and a substrate. The substrate, as shown prior in FIGS. 1-6 comprises an inner flexure formed from a plurality of first slots in the substrate, disposed proximate to a first peripheral portion of the substrate, and an outer flexure formed from a plurality of second slots in the substrate, disposed surrounding at least a portion of the plurality of first slots wherein a distal end of the separation membrane is disposed under the outer flexure, where a proximal end of the collection membrane is disposed under at least one of the outer flexure and inner flexure such that the proximal end of the collection membrane has an overlapping contact area with the distal end of the separation membrane, and where the outer flexure is configured to apply pressure on the separation membrane and collection membrane about the overlapping contact area. The kit also comprises a tourniquet for placing around a digit to apply the appropriate pressure, the tourniquet comprising a rubber band or other elastic material.

In certain embodiments, the kit may further comprise a lancet for producing the finger prick. In certain embodiments the lancet is a pressure-activated lancet. In certain other embodiments, the kit may also comprise instructions for use. In certain embodiments, the kit may also comprise a capillary or transfer tube for collecting the blood drop from the lanced or incised finger and subsequently dispensing the blood onto the device for separating and collecting plasma.

In certain embodiments the instructions may be sufficiently detailed as to provide methods that further facilitate blood collection and efficiency. For example the instructions may include parameters for preparing the hand and finger to insure proper blood flow including temperature and position, methods of applying the tourniquet to the finger, methods of sterilization, lancing, and actual blood collection. The instructions may further provide detail on using the plasma clip device.

For example an exemplary method, which would be included in instructions, may include a series of steps to prepare of the finger for sampling, applying the finger tourniquet, sterilization, lancing, blood collection, blood dispensing, and post-procedure storage.

For preparation, instructions may state for example; hand-warming is encouraged to stimulate blood flow prior to lancing. A preferable practice is to hold hands under warm water for approximately 2 minutes, but other possibilities include using a chemical heater (e.g. crystalline-activated pouch) or generating friction by rubbing the hands together vigorously. To achieve proper blood flow, hands should be positioned below the heart and muscles should be relaxed. This is typically achieved by seating the donor comfortably in a chair and loosely placing the arm on a low surface or table.

For applying the tourniquet, the instructions may state; select the donor's non-dominant hand (e.g. choose left hand if donor is right-handed) and ideally select the donor's middle finger. Alternative sites include the ring and index fingers. Loop a rubber band or equivalent tourniquet material around the last digit of the finger and then twist and continue to loop around the finger several times to create a tourniquet. Leave a loop available for easy removal. Pressure will build at the fingertip and may appear slightly red or engorged. It is advisable that the donor or an assistant holds and pulls on the free loop of the tourniquet during the procedure.

Instructions related to sterilization may include; choose a side of the fingertip and swipe with a sterilizing wipe or alcohol pad. Dry the area with a piece of sterile gauze.

For lancing, the instructions may include depending on the type and source of lancet provided; twist-off the protective cap of the lancet and place toward the side of the sterilized finger. Be careful to avoid the center of the fingertip as this may be calloused or contain a higher density of nerve endings that may increase pain sensation. Press down on the lancet until you hear a clicking noise. Pressure-activated lancets are will create an incision after the spring is engaged (clicking noise). Please abort the procedure if no clicking noise is heard, as the incision may be superficial, and begin again on a new finger (e.g. ring or index finger).

For blood collection, the instruction may include; Wipe away the first evidence of blood immediately after lancing. Then apply mild but constant pressure on the finger. Hold the self-filling capillary horizontal to the incision site and touch against a forming blood droplet (repeat for each droplet if blood flow is slow). Self-filling capillaries (e.g. Microsafe®, Safe-Tec Clinical Products, LLC, Ivyland Pa.) will self-fill to the black line printed on the plastic shaft and then self-stop. Do not press the plastic bulb during this step. When the collected blood reaches the black line and stops filling, withdraw pressure on the fingertip. Release the free loop of the rubber band to reduce the pressure of the finger tourniquet For blood dispensing, the instructions may include how to use and position the device which may be referred to by a number of names including for example a plasma collection device; Place the blood sampling device on a flat surface. If there is significant amount of blood on the outside of the capillary, wipe clean with sterile gauze. Immediately hold the filled capillary upright over the bottom of the plasma separation device. Dispense the collected blood by slowly and evenly pressing on the plastic bulb of the filled capillary. Keep the capillary fixed in one place over the bottom of the plasma separation device while dispensing. Discard the capillary when all blood is dispensed onto the plasma separation device.

Post-procedure instructions may include; let the blood sampling device sit undisturbed while the finger tourniquet is completely removed and the incision site is cleaned. Apply pressure to the incision using sterile gauze if bleeding persists. If necessary, raise the hand above the heart to assist in clotting. Observe the undisturbed blood sampling device approximately 5-10 minutes post-procedure and observe whether the blood drop is still raised on the filter and if filter still appears "wet." If no raised "wet" droplet of blood is observed and straw-color plasma starts to appear on the top of the plasma separation device then the sample can be placed back into a storage container, if provided. Label as appropriate. Maintain the sample at room temperature.

In certain embodiments graphical or actual pictures may be included to further illustrate the procedure.

EXPERIMENTAL

Several different parameters were tested under controlled conditions, including (1) type of lancet, (2) effect of milking, (3) finger selection, (4) tourniquet options, and (5) effect of residual ethanol on the finger after surface decontamination.

Figure 8:
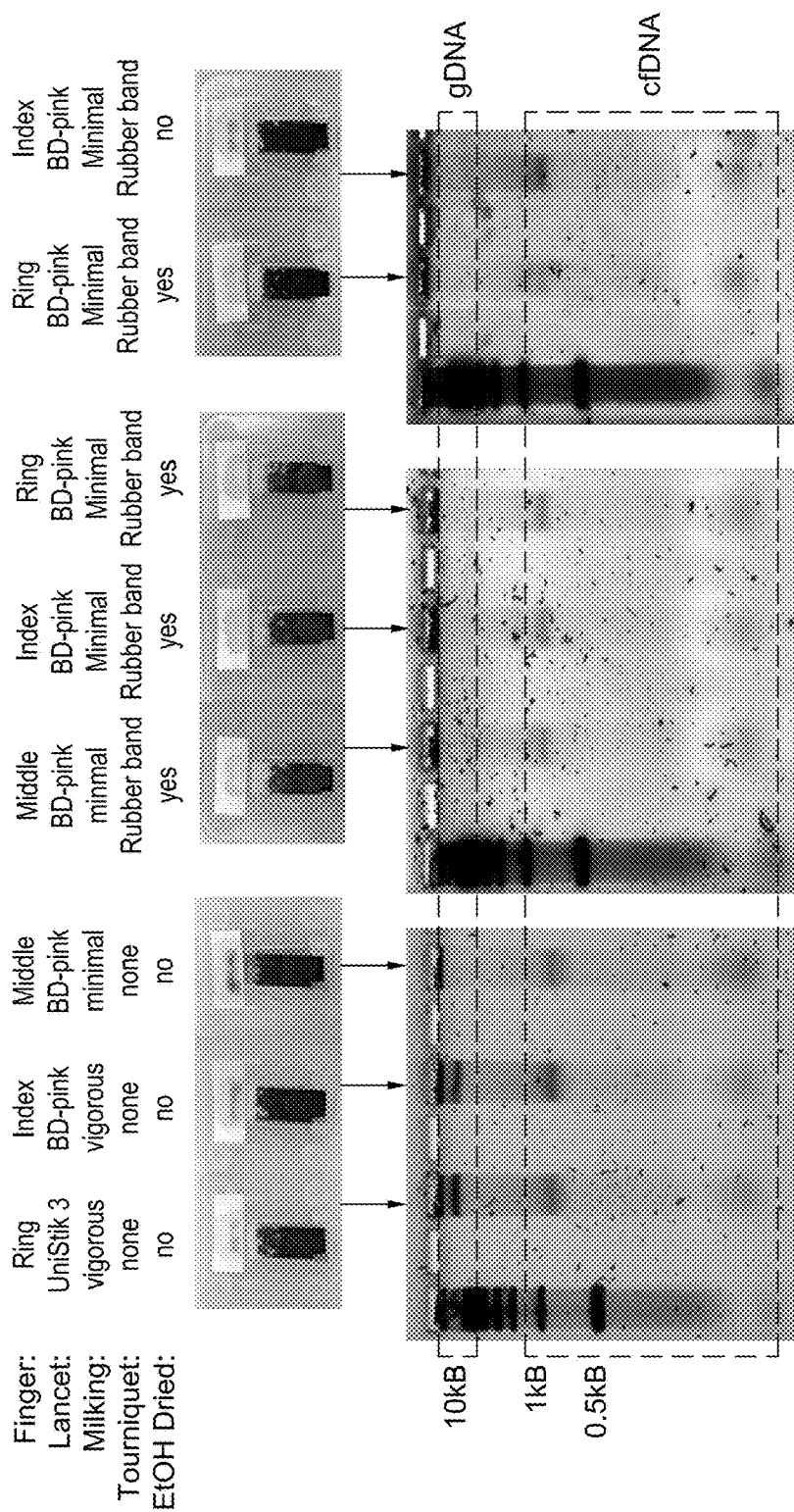
FIG. 8 depicts 2% gel electrophoresis analysis of cell-free plasma collected with or without use of a tourniquet.

To test these parameters, approximately 75 µl of finger prick blood was applied onto plasma separation devices fitted with glass fiber and cellulose membranes (for separating and storing plasma, respectively), and samples were allowed to dry to create dried plasma spots. Devices, with the blood and plasma spotted membranes, were stored at ambient temperature (but controlled humidity) for at least three (3) days. Cellulose strips containing dried plasma were slid-away from the plasma separation device and extracted using DNA Extractor® SP (Wako Chemicals USA, Inc. Richmond, Va.), and plasma DNA was analyzed by 2% gel electrophoresis (FIG. 8).

These finger prick tests revealed a number of novel learnings. First, pressure-activated lancets (e.g. Microtainer® Contact-Activated Lancets Pink, Becton, Dickinson and Company, Franklin Lakes, N.J.) showed better lancing efficiency than spring-activated lancets (e.g. UniStik®3, Owen Mumford, Oxford, United Kingdom). Second, vigorously milking the finger to acquire 75 µL of capillary blood resulted in significant genomic DNA contamination (depicted in the gel in FIG. 8 as high-molecular weight DNA>10 kB) presumably from the release of interstitial fluid. Surprisingly, it was found that building capillary pressure using a rubber band tourniquet eliminated gDNA contamination and allowed for isolation of pure cell-free DNA species (depicted in the gel in FIG. 7 as low-molecular weight DNA<1 kB) (FIG. 8). This tourniquet method also facilitated easier blood collection (regardless of finger selection), as originally reported by Mezitis and Pi-Sunyer (Mezitis and Pi-Sunyer, 1987, "Self-monitoring of blood glucose: Tourniquet method"). Lastly, inefficient drying of the finger after ethanol decontamination was found to contribute minor heme release (but not genomic DNA contaminants) within the dried plasma spot. This was effectively mitigated by fully drying the finger prior to lancing. Thus, these results established clinical feasibility for collecting cfDNA from finger prick blood using a simple tourniquet together with a membrane-based blood separator.

While only certain features of embodiments have been illustrated and described herein, many modifications and changes will occur to those skilled in the art. It is, therefore, to be understood that the appended claims are intended to cover all such modifications and changes as falling within the spirit of the invention.

The invention claimed is:

1. A method of separating and collecting a cell-free plasma sample that minimizes contamination with genomic DNA (Deoxyribonucleic Acid) from a donor, the method comprising:
    placing a tourniquet on a digit of the donor's hand to apply pressure;
    lancing the digit to create an incision in the digit;
    collecting blood from the incision;
    dispersing the collected blood onto a separation membrane wherein the separation membrane is in contact with a collection membrane and said separation and collection membranes only overlap at a portion of the collection membrane defined as an overlapping contact area for both said membranes, wherein both the separation membrane and the collection membrane are inserted into a substrate configured to provide overlap between said membranes at the defined overlapping contact area; and
    collecting the cell-free plasma sample on the defined overlapping contact area,
    wherein the collected cell-free plasma sample contains cell-free DNA and is substantially free of genomic DNA, and
    wherein the substrate further comprises:
    an inner flexure defined by a plurality of first slots in the substrate, disposed proximate to a first peripheral portion of the substrate;
    an outer flexure defined by a plurality of second slots in the substrate, disposed surrounding at least a portion of the plurality of first slots;
    wherein the inner flexure comprises a first distal end portion and the outer flexure comprises a second distal end portion overlapping with a fraction of the first distal end portion of the inner flexure, and
    means for holding and aligning the separation membrane to position along the inner flexure, said means located between the first peripheral portion and a first proximal end portion of the inner flexure.

2. The method of claim 1, wherein an overlapping contact distance of the overlapping contact area in the longitudinal direction is in a range from about 1 mm to about 2 mm.

3. The method of claim 1, further comprising: positioning the separation membrane and the collection membrane on the substrate and forming the overlapping contact area between the separation membrane and the collection membrane.

4. The method of claim 3, wherein forming the overlapping contact area further comprises forming the overlapping contact area between a distal end of the separation membrane and a proximal end of the collection membrane.

5. The method of claim 3, further comprising: applying a pressure at the overlapping contact area.

6. The method of claim 3, wherein the overlapping contact area is in a range of about 8 mm$^2$ to about 16 mm$^2$.

7. The method of claim 1, further comprising: separating the collected blood using the separation membrane and collecting the plasma sample using the collection membrane, wherein both separating and collecting are by a capillary flow.

8. The method of claim 1, where the tourniquet is an elastic material or a rubber band.

9. The method of claim 1, further comprising removing a first blood immediately after lancing while still applying pressure.

10. The method of claim 1, wherein the collecting step further comprises holding a capillary tube against the blood formed from the incision to collect the blood.

11. The method of claim 1, wherein the collecting step is carried out without milking the finger.

12. The method of claim 1,
    wherein the dispersing step further comprises applying pressure by an external force on the separation membrane and the collection membrane about the defined overlapping contact area.

* * * * *